United States Patent [19]

Bouchette et al.

[11] Patent Number: 4,781,974

[45] Date of Patent: Nov. 1, 1988

[54] ANTIMICROBIALLY ACTIVE WET WIPER

[75] Inventors: Michael P. Bouchette; Joseph H. Miller, both of Appleton, Wis.

[73] Assignee: James River Corporation, Richmond, Va.

[21] Appl. No.: 23,228

[22] Filed: Mar. 9, 1987

Related U.S. Application Data

[63] Continuation of Ser. No. 854,811, Apr. 23, 1986.

[51] Int. Cl.$^4$ .............................................. A61H 9/70
[52] U.S. Cl. .................................. 428/288; 15/104.93; 427/389.9; 427/421; 427/439; 428/290; 428/913; 604/360
[58] Field of Search ............... 428/288, 289, 290, 446, 428/452, 913; 15/104.93; 604/360; 427/389.9, 421, 439; 424/443, 414

[56] References Cited

U.S. PATENT DOCUMENTS

| | | | |
|---|---|---|---|
| 2,474,306 | 6/1949 | Doub | 260/212 |
| 2,702,780 | 2/1955 | Lerner | 167/84 |
| 3,138,533 | 6/1964 | Helm et al. | 167/84 |
| 3,227,614 | 1/1966 | Scheuer | 167/84 |
| 3,257,267 | 6/1966 | Hay | 162/159 |
| 3,264,172 | 8/1966 | Regotti | 162/161 |
| 3,567,118 | 3/1971 | Shepherd et al. | 424/28 |
| 3,624,224 | 11/1971 | Wei et al. | 424/28 |
| 3,728,213 | 4/1973 | Hinz | 424/28 |
| 3,860,709 | 1/1975 | Abbott et al. | 424/184 |
| 3,959,556 | 5/1976 | Morrison | 57/140 |
| 4,259,103 | 3/1981 | Malek et al. | 424/25 |
| 4,282,366 | 8/1981 | Fudy | 556/413 |
| 4,311,479 | 1/1982 | Fenn et al. | 8/495 |
| 4,343,853 | 8/1982 | Morrison | 428/233 |
| 4,394,378 | 7/1983 | Klein | 424/184 |
| 4,401,712 | 8/1983 | Morrison | 428/907 |
| 4,406,892 | 9/1983 | Fudy | 424/184 |
| 4,408,996 | 10/1983 | Baldwin | 424/184 |
| 4,737,405 | 4/1988 | Bouchette | 428/290 |

OTHER PUBLICATIONS

Steven F. Hayes et al., "How Antimicrobial Treatment Can Improve Nonwovens", American Dyestuff Reporter, Jun. 1984, pp. 35–45.

Primary Examiner—James J. Bell
Attorney, Agent, or Firm—Finnegan, Henderson, Farabow, Garrett & Dunner

[57] ABSTRACT

An antimicrobially active wet wiper and a method of making the wiper. The wet wiper has an antimicrobially active non-woven web that includes: (i) bonded fibers; (ii) a binder in an amount effective to bind the fibers; and (iii) a first antimicrobial agent that is substantive to the fibers and to the binder when the web is either wet or dry. The web is maintained in a wet condition in a liquid containing a second antimicrobial agent until use.

32 Claims, No Drawings

4,781,974

ANTIMICROBIALLY ACTIVE WET WIPER

This is a continuation of application Ser. No. 854,811, filed Apr. 23, 1986.

BACKGROUND OF THE INVENTION

The present invention relates to wet wipers and, more particularly, to an antimicrobially active wet wiper, to a method of making the wiper, and to a method of enhancing the antimicrobial activity of the wet wiper.

Wet wiper products require antimicrobial properties to destroy or inhibit the growth of various microorganisms, bacteria, yeasts, and molds. The most universally common method of achieving this control is by the use of chemical antimicrobial agents dispersed or dissolved in the liquid phase of the wet wiper. This method is generally satisfactory from an antimicrobial efficacy standpoint, but has some inherent disadvantages.

Namely, the nature of the chemicals used to achieve antimicrobial control often necessitates the use of various alcohols, surfactants, or other solubilizing agents to get sufficient quantities of the antimicrobial agents into solution and to allow a sufficient range of chemicals so as to impart a broad spectrum of antimicrobial control. The nature of the required chemicals and the complexity of the final liquid phase formulations inevitably result in residues being left behind on the skin of the user. Such residues may often prove harsh or irritating, thereby impeding the enjoyable use of the wet wiper product.

It has already been shown by Michael P. Bouchette in U.S. patent application Ser. No. 722,845, filed on Sept. 5, 1985 entitled "Antimicrobially Active, Non-Woven Web used in a Wet Wiper," and issued as U.S. Pat. No. 4,615,937 that a wet wipe product can be produced in which the antimicrobial is substantive to the wiper fabric or web and binder.

Although a recognized standard acceptable level of antimicrobial protection is associated with meeting the criteria set forth in the United States Pharmacopeia (U.S.P.) XIX 28 day challenge test, it is nonetheless advantageous to increase antimicrobial protection whenever it can be readily done without significantly affecting the product cost and/or the potential adverse consumer reaction. This potential adverse reaction can be due to any number of factors, including both perceived complexity of the chemical formulation and actual allergic response to the chemicals. Although a wet wiper cannot be protected against all organisms, while still providing a viable product for consumer use, it is desirable to expand the scope of antimicrobial protection such that potentially harmful user contamination due to unforeseen microbial contamination may be reduced or minimized. This results in an increase in the antimicrobial spectrum of resistance within the product.

SUMMARY OF THE INVENTION

The present invention achieves these goals and provides advantages over previous wet wipers. The present invention is an antimicrobially active wiper that overcomes the significant and inherent disadvantages present in previous wet wipers.

The wet wiper of the present invention has an antimicrobial agent that is substantive to the fibers and the binder of the non-woven web when the web is either wet or dry. This antimicrobial agent will not leave harmful residues on the user's skin. The wet wiper of the present invention is maintained in a liquid containing a second antimicrobial agent that acts as a preservative.

More particularly, the antimicrobially active the present invention has an antimicrobially active non-woven web. The web comprises (i) bonded fiber, ii a binder in an amount effective to bind the fibers, and (iii) a first antimicrobial agent that is substantive to the fibers and to the binder when the web is either wet or dry. This web is maintained in a wet condition in a liquid containing a second antimicrobial aqent until use.

The present invention also provides a method for makinq an antimicrobially active, wet wiper. In the method, an unbonded fibrous web is formed. An uncured binder and a first antimicrobial agent are then applied throughout the unbonded fibrous web. The first antimicrobial agent is substantive to the fibers of the web and to the binder when the web is either wet or dry. The binder is cured to bind the fibers together to form an antimicrobially active, non-woven web. The web is stored in a liquid containing a second antimicrobial agent to maintain the web in a wet condition until use.

Preferably, the substantive or first antimicrobial agent is an organo-silicon quaternary ammonium salt, such as a silylquaternary ammonium salt. Particularly preferred substantive antimicrobial agents are 3-(trimethoxysilyl) propyldidecylmethyl ammonium salt and 3-(trimethoxysilyl) propyloctadecyldimethyl ammonium salt. Preferably, the second antimicrobial agent that is present in the liquid is a naturally occurring organic acid capable of exhibiting antimicrobial properties, such as sorbic acid, citric acid, malic acid, or combinations thereof.

The foregoing and other features and advantages of the present invention will be made more apparent from the following description of the preferred embodiments.

DESCRIPTION OF THE PREFERRED EMBODIMENTS

In accordance with the present invention, the wet wiper has an antimicrobially active non-woven web. This non-woven web includes bonded fibers and a binder in an amount effective to bind the fibers. Although various synthetic and natural fibers known in the art can be effectively used, the preferred fibers are celulosic fibers and, more preferably, wood pulp fibers. The cellulosic fibers, such as wood pulp fibers, can be chemically treated prior to the formation of the web or fabric, if desired. Examples of wood pulp fibers include various mechanical and chemical pulp fibers, such as cedar fibers, Southern pine fibers, spruce fibers, and hemlock fibers. The particular fibers may be specifically selected to enhance properties such as texture (soft, wooly or fluffy), porosity, caliper, brightness, strength, and so on. Alternatively, the fibers can be a combination of natural and synthetic fibers, or synthetic fibers alone, depending upon the final attributes sought and the method of forming the web.

The weight of the fibers, such as cellulosic fibers, used to form the unbonded fibrous web can vary depending upon the ultimate non-woven web that is produced. Typically, the weight of the fibers forming the web will vary within the range of about 5 lbs. per 3000 $ft^2$ to about 60 lbs. per 3000 $ft^2$.

Various web or fabric forming techniques known in the art can be effectively used to form the unbonded fibers. The web can be formed by nonwoven techniques, such as air-laying the web or wet-laying the web. One type of apparatus for air forming fibers is shown in U.S. Pat. No. 4,292,271 to Buob et al. Other non-woven manufacturing techniques, such as melt blown, spunbonded, needle punched, and spun laced, may also be used.

Various binders known in the art can be used to bind the fibers together. A preferred binder is a polymeric binder, such as a latex binder. Acceptable latex binders include acrylate emulsions, butadiene-styrene emulsions, ethylene vinyl acetate emulsions and acrylonitrile-butadiene emulsions. An especially effective latex binder is ethylene vinyl acetate, which is sold under the trademark AIRFLEX A-410 by Air Products, Inc. of Allentown, Pa. The binder can also include a mixture of anionic and nonionic binders, such as the ethylene vinyl acetate binder sold under the trademark AIRFLEX A-106 by Air Products, Inc. and the ethylene acetate binder sold under the trademark HA-8 by Rohm & Haas of Philadelphia, Pa.

The amount of the binder that is to be applied to the fibers depends, in part, upon the type of fibers, such as cellulosic, and the type of the first antimicrobial agent being used in the non-woven web. Typically, the amount of the binder applied to the fibers varies within the range of about 5% to about 30% of total web weight. Similarly, the amount of solids in the binder, as applied to the web, especially in a latex binder, depends, inter alia, on the weight of the fibers in the non-woven web. Generally, latex binders having from about 5% to about 25% application solids content are used. Of course, one of ordinary skill in the art can select the particular binder, the amount of the binder used, and the amount of solids present in the binder, depending upon, in part, the type of fibers that are to be bound and the first antimicrobial agent being used. The binder is applied to the fibers by various techniques known in the art, such as spraying, foaming, or padding.

In accordance with the present invention, the non-woven web of the wet wiper has a first antimicrobial agent that is substantive to the fibers and to the binder when the web is either wet or dry. The first antimicrobial agent is preferably uniformly distributed on the fibers. The first or substantive antimicrobial agent is selected to be substantive to both the fibers of the web and to the binder when the web is either wet or dry. As used herein, an antimicrobial agent is substantive to the fibers and the binder if the antimicrobial agent attaches directly to the fibers of the web and to the binder without the need for an adhesive substance. Consequently, substantive antimicrobial agents do not substantially diffuse from either the fibers or the binder used to bind the fibers together.

The first antimicrobial agent is selected to be substantive to the binder in addition to being substantive to the fibers of the non-woven web. Hence, such an antimicrobial agent attaches directly to the binder and the fibers of the non-woven web without the need for an adhesive substance. Likewise, the ionic character of the binder is carefully chosen so that the antimicrobial active agent is usually substantially inert with respect to the binder to prevent ionic interaction of the antimicrobial agent and the binder.

Preferred first or substantive antimicrobial agents to be applied to the fibers and binder of the non-woven web are organosilicon quaternary ammonium salts, such as a silyl-quaternary ammonium salt. Preferred organosilicon quaternary ammonium salts are 3-(trimethoxysilyl) propyldidecylmethyl ammonium salts, such as 3-(trimethoxysilyl) propyldidecylmethyl ammonium chloride, and 3-(trimethoxysilyl) propyloctadecyldimethyl ammonium salts, such as 3-(trimethoxysilyl) propyloctadecyldimethyl ammonium chloride.

Examples of commercially available organo-silicon quaternary ammonium salts useful as the first or substantive antimicrobial agent in the present invention are sold under the trademarks SIQUAT 1977 by Sanitized, Inc. and DOW CORNING 5700 by the Dow Chemical Co. Another substantive antimicrobial agent that is not an organo-silicon quaternary ammonium salt is N-(2-methyl-1-napthyl maleimide) sold under the trademark Vinyzene 129 by Morton Thioxol, Ventron Division.

The first antimicrobial agent is preferably applied to the fibers of the non-woven web prior to or simultaneously with the application of the binder. Although various amounts of the first antimicrobial agent are applied to the non-woven web depending upon, in part, the fibers selected and the particular binder used, the amount of the first antimicrobial active agent is typically in the range of about 0.25% to about 3% of the total web weight. A particularly preferred amount of the substantive or first antimicrobial agent is about 1% to about 2% of the total web weight. When the first antimicrobial agent is applied to the non-woven web simultaneously with the binder, the first antimicrobial agent is preferably about 0.5% to about 10% of the binder volume and, most preferably, about 3.5% of the binder volume.

The first antimicrobial agents can be prepared by various techniques known in the art. For example, U.S. Pat. Nos. 4,406,892 to Eudy, 4,282,366 to Eudy, 4,394,378 to Klein, and 4,408,996 to Baldwin describe various organo-silicon quaternary ammonium compounds, especially silyl quaternary ammonium compounds, and methods of preparing these compounds. Likewise, articles in the scientific literature, such as Walters et al., Algicidal Activity of a Surface-Bonded Organosilicon Quaternary Ammonium Chloride, 25 *Applied Microbiology,* 253—256 (1972) and Isquith et al. Surface-Bonded Antimicrobial Activity of an Organosilicon Quaternary Ammonium Chloride, 24 *Applied Microbiology.* 859–863 (1972), also disclose methods of making various organosilicon quaternary ammonium compounds. Thus, the skilled artisan can readily select a method of preparing the desired first antimicrobial agent, such as an organosilicon quaternary ammonium compound.

The uncured binder and the first antimicrobial agent are applied to the unbonded fibers in a manner that allows the binder and the first antimicrobial agent to be present throughout the unbonded fibrous web and, hence, substantially uniformly distributed on the fibers. Accordingly, substantially all of the unbonded fibers of the web are to be contacted with the uncured binder and the first antimicrobial agent during this application process.

Various application methods and apparatus, known in the arts can be readily selected by the skilled artisan. For example, the uncured binder and the first antimicrobial agent are sprayed onto unbound fibers, such as cellulosic fibers, that have been airlaid on a foraminous support. Similarly, the uncured binder and the first antimicrobial agent can be contained in a bath through which the unbonded fibers pass. Other methods and apparatus include foaming and printing.

The binder material is then cured to bind the fibers together to form an antimicrobial, non-woven web.

Various curing techniques known in the art, such as infra-red radiation, electron beam, and forced hot air, can be effectively selected and used by the skilled artisan to achieve the proper degree of binder cure.

As a result, an antimicrobially active, non-woven web is provided. The non-woven web has bonded fibers; a binder substantially uniformly distributed on the fibers, the binder being present in an amount effective to bind the fibers; and a first antimicrobial agent being substantive to the fibers and to the binder when the web is either wet or dry.

In accordance with the present invention, the antimicrobially active, non-woven web is stored in a liquid containing a second antimicrobial agent to maintain the web in a wet condition in the liquid until use. The liquid has a second antimicrobial agent in it, typically mild, naturally occurring selected organic acids.

The storage liquid for the wet wiper preferably is water and, most preferably, pure water having as its only ingredient the second antimicrobial agent. Such a storage liquid containing the second antimicrobial agent is safe for skin contact and a highly effective antimicrobial control that kills a broad spectrum of microorganisms. In addition, the preferred mild naturally occurring organic acids are edible and, typically, are found in or extracted from foodstuffs, thereby also decreasing any likelihood of adverse allergenic skin reaction of the user.

The second antimicrobial agent is preferably an organic acid that is capable of exhibiting antimicrobial properties. The skilled artisan can select appropriate antimicrobial organic acids that are compatible with the first or substantive antimicrobial agent and that can be safely used in the liquid storage of the wet wiper without providing an irritating or harmful residue on the user's skin. Preferred naturally occurring organic acids include citric acid, sorbic acid, malic acid, and combinations thereof. An additional mild, but not naturally occurring, organic acid that may be used is ethylenediaminetetraacetic acid. Preferably, the organic acid is present in the liquid in the range of about 0.05 wt % to about 2.0 wt % of the total liquid and, most preferably, in the range of about 0.3 wt % to about 1.5 wt % of the total liquid.

An especially preferred antimicrobial agent for the storage liquid is a mixture of sorbic acid and citric acid. Preferably, this mixture has about 0.01% to about 0.20% weight sorbic acid and about 0.1% to about 0.5% weight citric acid, the weight percents being based upon the liquid. An example of an especially effective second antimicrobial agent mixture is 0.075% weight sorbic acid and 0.375% weight citric acid.

In the case of the non-woven web, the criteria for proper selection of the antimicrobial agent include substantivity, antimicrobial activity, and safety, such that the wet wiper is safe for use on human skin and eyes. In the case of the antimicrobial agents in the liquid load, the criteria are antimicrobial activity, non-formaldehyde releasers, and mild so as to be safe for use on human skin and eyes and, preferably, naturally occurring. It may also be desirable that the liquid load antimicrobial agents are edible, in case the wet wiper is used for wiping the face or mouth.

The method of the present invention produces an antimicrobially active, wet wiper. Initially, the present method forms an unbonded fibrous web. An uncured binder and a first antimicrobial agent are then applied throughout the unbonded fibrous web, with the first antimicrobial agent being substantive to both the fibers of the web and to the binder when the web is either wet or dry. After application of the binder and the first antimicrobial agent, the binder is cured to bind the fibers together to form an antimicrobially active, non-woven web. The web is then stored in a liquid containing a second antimicrobial agent to maintain the web in a wet condition until use.

The following is an example of the present invention, and it is intended to be merely exemplary.

EXAMPLE

An antimicrobially active, non-woven web was prepared. Unbonded cellulosic fibers were air-laid to produce an unbonded cellulosic fiber web of 30 pounds per ream. An uncured latex binder having 4.2% of antimicrobial agent based on latex solids was applied throughout the cellulosic web to bring the final, bonded, treated web basis weight to 45 pounds per ream. The binder was then cured to bind the cellulosic fibers together to form an antimicrobial active, non-woven web. The web was then cut into several pieces that were stored in different storage liquids.

Web A was stored in a liquid consisting of water that did not contain any antimicrobial agent. Web B was stored in a liquid consisting of water containing 0.075% weight sorbic acid. Web C was stored in a liquid of water containing 0.375% weight citric acid. Web D was stored in a liquid of water containing 0.075% weight sorbic acid and 0.375% weight citric acid.

The resulting air-laid, non-woven wet wipers were tested to determine their antimicrobial activity. Specifically, each wet wiper was tested to determine its effect on reduction and inhibition of five United States Pharmacopeia (U.S.P.) antimicrobial preservative effectiveness challenge organisms, plus the addition of *Pseudomonas capacia*, a likely contaminant in wet wipers.

Each wet wiper was subjected to *Aspergillus niger, Candida albicans, Staphylococcus aureus, Pseudomonas aeruqinosa, Escherichia coliformia,* and *Pseudomonas cepacia* with total inoculation levels of $10^5$ to $10^6$ microorganisms/ml. Subsequent total plate counts were taken at intervals of 10, 30, 60, and 120 minutes for bacteria, and 1, 4, 8, and 24 hours for fungi. The results are provided in Table 1.

TABLE NO. 1

| Wet Wiper Lotion Additives | | Time | *E. coli* | *S. aureus* | *P. aeruginosa* | *P. cepacia* | TIME | *C. albicans* | *A. niger* |
|---|---|---|---|---|---|---|---|---|---|
| A | | 10 min. | $1.3 \times 10^5$ | $1.2 \times 10$ | $1.7 \times 10^4$ | $6.2 \times 10^3$ | 1 hr. | <10 | $4.7 \times 10^3$ |
| | | 30 min. | $2.4 \times 10^5$ | $9.1 \times 10^4$ | $2.0 \times 10^4$ | $5.4 \times 10^3$ | 4 hrs. | <10 | $6.2 \times 10^2$ |
| | | 60 min. | $2.3 \times 10^5$ | $9.1 \times 10^4$ | $1.6 \times 10^4$ | $4.4 \times 10^3$ | 8 hrs. | <10 | $2.1 \times 10^2$ |
| | | 120 min. | $2.6 \times 10^4$ | $5.0 \times 10^4$ | $3.0 \times 10^3$ | $7.0 \times 10^2$ | 24 hrs. | <10 | $1.8 \times 10^3$ |
| B | sorbic acid | 10 min. | $2.2 \times 10^5$ | $2.0 \times 10^5$ | $1.3 \times 10^5$ | $6.8 \times 10^3$ | 1 hr. | 50 | $6.0 \times 10^3$ |
| | | 30 min. | $1.8 \times 10^5$ | $8.0 \times 10^4$ | $4.5 \times 10^4$ | $6.2 \times 10^3$ | 4 hrs. | <10 | $3.8 \times 10^3$ |
| | | 60 min. | $1.7 \times 10^5$ | $1.9 \times 10^5$ | $3.5 \times 10^4$ | $5.2 \times 10^3$ | 8 hrs. | <10 | $3.1 \times 10^3$ |
| | | 120 min. | $1.7 \times 10^4$ | $2.5 \times 10^4$ | $8.5 \times 10^3$ | $1.0 \times 10^3$ | 24 hrs. | <10 | $3.0 \times 10^2$ |

TABLE NO. 1-continued

| Wet Wiper Lotion Additives | | Time | E. coli | S. aureus | P. aeruginosa | P. cepacia | TIME | C. albicans | A. niger |
|---|---|---|---|---|---|---|---|---|---|
| C | citric acid | 10 min. | $2.5 \times 10^5$ | $1.6 \times 10^5$ | $5.8 \times 10^2$ | 30 | 1 hr. | $3.8 \times 10^2$ | $1.2 \times 10^4$ |
|   |   | 30 min. | $4.7 \times 10^4$ | $8.0 \times 10^4$ | 30 | <10 | 4 hrs. | <10 | $2.4 \times 10^3$ |
|   |   | 60 min. | $1.0 \times 10^4$ | $8.4 \times 10^3$ | <10 | <10 | 8 hrs. | <10 | $3.2 \times 10^2$ |
|   |   | 120 min. | $4.2 \times 10^3$ | $9.6 \times 10^2$ | <10 | <10 | 24 hrs. | <10 | $4.2 \times 10^2$ |
| D | sorbic acid & citric acid | 10 min. | $2.0 \times 10^4$ | $2.4 \times 10^5$ | <10 | <10 | 1 hr. | $8.7 \times 10^2$ | $1.5 \times 10^4$ |
|   |   | 30 min. | $2.5 \times 10^4$ | $1.6 \times 10^5$ | <10 | <10 | 4 hrs. | <10 | $1.0 \times 10^3$ |
|   |   | 60 min. | — | $1.1 \times 10^3$ | <10 | <10 | 8 hrs. | <10 | $5.5 \times 10^2$ |
|   |   | 120 min. | $2.0 \times 10^2$ | $2.2 \times 10^2$ | <10 | <10 | 24 hrs. | <10 | 30 |

Especially excellent antimicrobial results were obtained for web D that was stored in a liquid of water containing both sorbic acid and citric acid. Such a wet wiper was especially effective in attacking *E. coli*, *P. aeruginosa*, and *A. niger* microorganisms for both the rate of kill and demonstrating superior microorganisms count reduction per unit time in comparision to a wiper consisting of a web treated with a substantive antimicrobial plus pure water as the wetting solution, or a web treated with the substantive antimicrobial plus water and citric acid as the antimicrobial wetting solution. In addition, sample D offered superior numerical microorganism plate count reduction for *E. coli*, and *A. niger* when compared to any of the other test systems.

Other embodiments of the invention will be apparent to one skilled in the art from a consideration of the specification or with the practice of the invention disclosed herein. It is intended that the specification and example be considered as exemplary only with the true scope and spirit of the invention being indicated by the claims.

What is claimed is:

1. An antimicrobially active wet wiper comprising:
   (a) an antimicrobially active non-woven web comprising:
      (i) bonded fibers;
      (ii) a binder in an amount effective to bind the fibers;
      (iii) a first antimicrobial agent being substantive to the fibers and to the binder when the web is either wet or dry; and
   (b) a liquid containing a second antimicrobial agent, the web being maintained in a wet condition in the liquid until use.
2. The wet wiper of claim 1, wherein the second antimicrobial agent is an organic acid capable of exhibiting antimicrobial properties.
3. The wet wiper of claim 2, wherein the organic acids are naturally occurring.
4. The wet wiper of claim 2, wherein the organic acids are edible.
5. The wet wiper of claim 2, wherein the organic acid is selected from the group consisting of citric acid, sorbic acid, ethylenediaminetetraacetic acid, malic acid, and combinations thereof.
6. The wet wiper of claim 1, wherein the liquid is water.
7. The wet wiper of claim 1, wherein the second antimicrobial agent comprises a mixture of about 0.01% to about 0.20% weight sorbic acid and about 0.1% to about 0.5% weight citric acid, the weight percents being based upon the liquid.
8. The wet wiper of claim 1, wherein the fibers are selected from the group consisting of cellulosic fibers, synthetic fibers, and combinations thereof.
9. The wet wiper of claim 1, wherein the binder is a polymeric binder.
10. The wet wiper of claim 9, wherein the polymeric binder is a latex binder.
11. The wet wiper of claim 1, wherein the first antimicrobial agent is an organo-silicon quaternary ammonium salt.
12. The wet wiper of claim 1, wherein the first antimicrobial agent is selected from the group consisting of a 3-(trimethoxysilyl) propyldidecylmethyl ammonium salt and 3-(trimethoxysilyl) propyloctadecyldimethyl ammonium salt.
13. An antimicrobially active wet wiper comprising:
   (a) an antimicrobially active non-woven web comprising:
      (i) bonded cellulosic fibers;
      (ii) a polymeric binder in an amount effective to bind the fibers;
      (iii) a antimicrobial agent being substantive to the fibers and to the binder when the web is either wet or dry; and
   (b) a liquid containing an antimicrobial organic acid, the web being maintained in a wet condition in the liquid until use.
14. The wet wiper of claim 13, wherein the organic acid is selected from the group consisting of citric acid, sorbic acid, ethylenediaminetetraacetic acid, malic acid, and combinations thereof.
15. The wet wiper of claim 14, wherein the antimicrobial agent is an organo-silicon quaternary ammonium salt.
16. The wet wiper of claim 15, wherein the organo-silicon quaternary ammonium salt is selected from the group consisting of 3-(trimethoxysilyl) propyldidecylmethyl ammonium salt and 3-(trimethoxylsilyl) propyloctadecyldimethyl ammonium salt.
17. The wet wiper of claim 13, wherein the organic acid is selected from the group consisting of sorbic acid, citric acid and combinations thereof.
18. The wet wiper of claim 17, wherein the liquid is water.
19. The wet wiper of claim 18, wherein the polymeric binder is a latex binder.
20. The wet wiper of claim 19, wherein the organic acid comprises a mixture of about 0.01% to about 0.20% weight sorbic acid and about 0.1% to about 0.5% weight citric acid, the weight percents being based upon the liquid.
21. The wet wiper of claim 20, wherein the sorbic acid is present in about 0.075% weight and the citric acid is present in about 0.375% weight.
22. The wet wiper of claim 13, wherein the antimicrobial agent is present in an amount in the range of about 0.25% to about 3% of the total web weight.

23. The wet wiper of claim 13, wherein the organic acid is present in the liquid in the range of about 0.3% to about 1.5% of the total liquid.

24. A method for preparing an antimicrobially active wet wiper comprising the steps of:
(a) forming an unbonded fibrous web;
(b) applying throughout the unbonded fibrous web an uncured binder and a first antimicrobial agent, the first antimicrobial agent being substantive to the fibers of the web and to the binder when the web is either wet or dry;
(c) curing the binder to bind the fibers together to form an antimicrobially active, non-woven web; and
(d) storing the web in a liquid containing a second antimicrobial agent to maintain the web in a wet condition until use.

25. The method of claim 24, wherein the second antimicrobial agent is a naturally occuring organic acid.

26. The method of claim 25 wherein the organic acid is selected from the group consisting of citric acid, sorbic acid, malic acid, and combinations thereof.

27. The method of claim 24 wherein the fibers are selected from the group consisting of cellulosic fibers, synthetic fibers, and combinations thereof.

28. The method of claim 24 wherein the first antimicrobial agent is an organo-silicon quaternary ammonium salt.

29. The method of claim 24, wherein the first antimicrobial agent is selected from the group consisting of 3-(trimethoxyiilyl) propyldidecylmethyl ammonium salt and 3-(trimethoxysilyl) propyloctadecyldimethyl ammonium salt.

30. The method of claim 24, wherein the amount of the first antimicrobial agent applied to the web is in the range of about 0.25% to about 3% of the total web weight.

31. The method of claim 24, wherein the amount of the binder applied to the web is in the range of about 5% to about 50% of the total web weight.

32. The method of claim 24, wherein the amount of the second antimicrobial agent present in the liquid is in the range of about 0.3% to about 1.5% of the total liquid.

* * * * *